(12) United States Patent
Beppu et al.

(10) Patent No.: US 8,492,442 B2
(45) Date of Patent: Jul. 23, 2013

(54) MEDICINAL COMPOSITION, FOOD OR DRINK HAVING EFFECT OF ENHANCING PARASYMPATHETIC NERVOUS ACTIVITY

(75) Inventors: Yoshinori Beppu, Mishima-gun (JP); Nobuo Tsuruoka, Mishima-gun (JP); Hajime Komura, Mishima-gun (JP); Katsuya Nagai, Minoh (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 718 days.

(21) Appl. No.: 12/593,468

(22) PCT Filed: Mar. 28, 2008

(86) PCT No.: PCT/JP2008/056076
§ 371 (c)(1),
(2), (4) Date: Sep. 28, 2009

(87) PCT Pub. No.: WO2008/120713
PCT Pub. Date: Oct. 9, 2008

(65) Prior Publication Data
US 2010/0150891 A1     Jun. 17, 2010

(30) Foreign Application Priority Data
Mar. 30, 2007  (JP) .................................. 2007-092528

(51) Int. Cl.
*A01N 31/00*  (2006.01)
*A61K 31/10*  (2006.01)
*C07C 63/00*  (2006.01)
*C07C 65/00*  (2006.01)

(52) U.S. Cl.
USPC .......................................... 514/713; 562/405

(58) Field of Classification Search
None
See application file for complete search history.

(56) References Cited

U.S. PATENT DOCUMENTS

| 5,648,389 A | 7/1997 | Gans et al. |
| 6,596,301 B1 | 7/2003 | Masuyama et al. |
| 2004/0013706 A1 | 1/2004 | Baur et al. |

FOREIGN PATENT DOCUMENTS

| JP | 04-352720 | 12/1992 |
| JP | 9-2959 | 1/1997 |
| JP | 10-45610 | 2/1998 |
| JP | H10-502944 | 3/1998 |
| JP | 10-139674 | 5/1998 |
| JP | 2004-510740 | 4/2004 |
| JP | 04891255 B2 | 3/2012 |

OTHER PUBLICATIONS

Yamano et al. (Life Sciences 2006, 79, 1963-1967).*
Naruszewicz et al. (The American Journal of Clinical Nutrition 2002, 76, 1249-1255).*
Tanida et al., "Effects of intraduodenal injection of *Lactobacillus johnsonii* La1 on renal sympathetic nerve activity and blood pressure in urethane-anesthetized rats," Neuroscience Letters, 389 (2005) pp. 109-114.
Strom et al., "Co-cultivation of Antifungal *Lactobacillus plantarum* MiLAB 393 and *Aspergillus nidulans*, Evaluation of Effects on Fungal Growth and Protein Expression" FEMS Microbiology Letters, 2005, vol. 246, No. 1, pp. 119-124.
Valerio et al., "Production of Phenyllactic Acid by Lactic Acid Bacteria: An Approach to the Selection of Strains Contributing to Food Quality and Preservation", FEMS Microbilology Letters, 2004, vol. 233, No. 2, pp. 289-295.
Makras et al., "Kinetic Analysis of the Antibacterial Activity of Probiotic Lactobacilli Towards *Salmonella enterica* Serovar Typhimurium Reveals a Role for Lactic Acid and Other Inhibitory Compounds", Research in Microbiology, vol. 157, Issue 3, Apr. 2006, pp. 241-247.
Nagai et al., "Jiritsu Shinkei Katsudo Sokutei ni yoru Aroma Seihin, Kenko Shokuhin Oyobi Yakuzai no Kaihatsu Gijutsu [3] II Oyohen (2)-(1) Shokuhin ya Yakuzai no Jiritsu Shinkei to Shintai Kino ni Ataerru Eikyo: Kenko Shokuhin to Yakuzai Kaihatsu eno Oyo", Food & Packaging, 2006, vol. 47, No. 9, pp. 544-550. (in Japanese).
Nagai et al., "Jiritsu Shinkei Katsudo Sokutei ni yoru Aroma Seihin, Kenko Shokuhin Oyobi Yakuzai no Kaihatsu Gijutsu [4] II Oyohen (2)-(2) Shokuhin ya Yakuzai no Jiritsu Shinkei to Shintai Kino ni Ataerru Eikyo: Kenko Shokuhin to Yakuzai Kaihatsu eno Oyo", Food & Packaging, 2006, vol. 47, No. 10, pp. 602-607. (in Japanese).
International Search Report mailed May 1, 2008 in PCT/JP2008/056076 filed Mar. 28, 2008.

* cited by examiner

*Primary Examiner* — Jeffrey S. Lundgren
*Assistant Examiner* — Michael Schmitt
(74) *Attorney, Agent, or Firm* — Drinker Biddle & Reath LLP (57) ABSTRACT

It is intended to provide a safe composition for treating a disease or condition relating to autonomic nervous activity which has an autonomic nervous control effect; in particular, an effect of enhancing parasympathetic nervous activity. Thus, a medicinal composition, a food or a drink containing L-phenyl lactic acid and/or D-phenyl lactic acid and having an autonomic nervous control effect is provided.

11 Claims, 2 Drawing Sheets

MEDICINAL COMPOSITION, FOOD OR DRINK HAVING EFFECT OF ENHANCING PARASYMPATHETIC NERVOUS ACTIVITY

CROSS REFERENCE TO RELATED APPLICATIONS:

This application is the National Stage of International Application No. PCT/JP2008/056076, filed Mar. 28, 2008, and claims benefit of Japanese Application No. 2007-092528, filed Mar. 30, 2007, which are incorporated herein in their entirety.

TECHNICAL FIELD

This invention relates to a medicinal composition, a food or a drink which contains phenyl lactic acid and has an autonomic nervous control effect. Further, it relates to the medicinal composition, food or drink as described above wherein phenyl lactic acid is L-phenyl lactic acid and/or D-phenyl lactic acid. Further, it relates to the medicinal composition, food or drink as described above, which has an effect of enhancing parasympathetic nervous activity, and is to be used for treating a disease or condition relating to autonomic nervous activity.

BACKGROUND ART

To maintain the homeostasis, a living body has the autonomic nervous system, the endocrine system and the immune system. Among these systems, the autonomic nervous system is relatively free from the cerebral control and acts automatically without being consciously controlled, which is the origin of the name. It mainly controls visceral functions. The autonomic nervous system comprises the sympathetic nervous system and the parasympathetic nervous system and is controlled based on a balance between these two systems. When the body is in action, the sympathetic nervous activity become predominant and the whole body is in a state of tension. On the contrary, when the parasympathetic nervous activity become predominant, the tension is loosened and the body is relaxed (Non-Patent Document 1). Sympathetic hyperactivity causes pupil dilation, tachycardia, a rise in blood pressure, substance metabolism, hyperglycemia and so on. Parasympathetic hyperactivity causes activation of the digestion and absorption system, secretion of sweat and saliva and so on. It is also known that the autonomic nervous activity relate to control of the white adipose tissue and the brown adipose tissue functions. Namely, the white fat tissue function is controlled by the sympathetic nerve and hormones in the blood, while the brown fat tissue function is controlled mainly by the sympathetic nerve (Non-Patent Document 2).

Disturbance of the balance in autonomic nervous activity leads to health troubles such as indefinite complaint (Non-Patent Document 2). As countermeasures against health troubles focusing on the autonomic nervous activity, there have been disclosed, for example, relaxing via the enhancement of parasympathetic nervous activity with the use of a rutaceous or eucalyptus essential oil (Patent Document 1), an aroma therapy for enhancing parasympathetic nervous activity by using 4-methoxystyrene (Patent Document 2), promotion of lacrimation by enhancing on the parasympathetic nervous activity with the use of a peptide (Patent Document 3) and a sympathomimetic inhibitor using an n-3 higher unsaturated fatty acid which is efficacious against autonomic imbalance such as erythrophobia and anxiety neurosis (Patent Document 4).

On the other hand, concerning phenyl lactic acid, which is known as occurring in two kinds of optical isomers, the antibacterial and antifungal effects have been merely known hitherto. That is, phenyl lactic acid is known as being produced by microorganisms belonging to the genus *Lactobacillus*, showing an antifungal activity on *Aspergillus niger*, etc., showing an increase in the concentration thereof in a culture supernatant by addition of phenylalanine during the culture (Non-Patent Document 3). Further, it is known that phenyl lactic acid produced by use of a lactic acid bacterium exerts an antibacterial effect on pathogenic *Escherichia coli* O-157 and methicillin-resistant *Staphylococcus aureus* (Patent Document 5) and so on.

Patent Document 1: JP-A-2005-272445
Patent Document 2: JP-A-2004-131436
Patent Document 3: JP-A-H11-209294
Patent Document 4: JP-A-2004-067537
Patent Document 5: JP-A-2000-300284
Non-Patent Document 1: Toshio Hagihara, et al., Iwanami Koza, Gendai Igaku no Kiso, vol. 4, Seitai no Chousetsu Shisutemu, 1999
Non-Patent Document 2: Tomifusa Kuboki, Igaku no Ayumi, vol. 181, No. 12, 1013-1015, 1997
Non-Patent Document 3: FEMS microbiology Letters 233: 289-295, 2004

DISCLOSURE OF THE INVENTION

Problems that the Invention is to Solve

There are a large number of autonomic nervous disorders, and health disorders caused thereby; for example, indefinite complaint. However, it has been a common practice to separately treat these disorders, and no attempt has been made so far to control the autonomic nervous activity per se that are the fundamental cause of these disorders. Although each symptom can be temporarily alleviated by such a symptomatic treatment, there still remains a high risk of recurrence or the onset of another symptom caused by autonomic nervous disorders. Thus, there have been required drugs, foods and drinks whereby the autonomic nervous activity per se, i.e., the fundamental cause can be controlled.

Moreover, there are such problems that a desired effect, and minimal side effects and high safety should be established at the same time, and that a process for synthesizing a drug involves additional step(s), and the thus synthesized drug should be processed into a form assuring easy intake thereof such as tablets, which brings about another problem; high cost. Under these circumstances, there has been a strong need for a substance having an autonomic nervous control effect which can be obtained from a natural material occurring in nature via a simple process.

An object of the present invention is to provide a medicinal composition, a food and a drink which has an autonomic nervous control effect, in particular, an effect of reducing sympathetic nervous activity and an effect of enhancing parasympathetic nervous activity and is useful in treating a disease or condition relating to autonomic nervous activity.

Means for Solving the Problems

It has been confirmed that cells of a specific lactic acid bacterium can regulate sympathetic nervous activity of the kidney and enhance parasympathetic nervous activity of the stomach (Tanida M, et al., Neuroscience Letters 389:109-114, 2005).

To achieve the object as described above, the present inventors conducted intensive studies and found that phenyl lactic acid is contained in a culture supernatant of a specific lactic acid bacterium, and that L-phenyl lactic acid is contained therein as the major component between the two optical isomers thereof, by using the direct effects thereof on the rat autonomic nervous activity as an indication. Subsequently, they conducted experiments using rats to examine the individual effects of L-phenyl lactic acid and D-phenyl lactic acid on kidney sympathetic nervous activity, blood pressure and vagal (parasympathetic) nervous activity of the stomach, thereby completing the present invention.

Accordingly, the present invention relates to a medicinal composition, a food or a drink which contains a clinically effective amount of a compound (phenyl lactic acid) represented by the following formula (1):

[Chemical formula 1]

formula (I)

and a pharmaceutically or nutritionally acceptable additive and has an autonomic nervous control effect.

The invention further relates to the medicinal composition, food or drink as described above wherein the compound of the formula (1) is represented by the following formulae:

[Chemical formula 2]

(namely, D-phenyl lactic acid and/or L-phenyl lactic acid).

The invention further relates to the medicinal composition, food or drink as described above which is to be used for treating a disease or condition relating to autonomic nervous activity.

The invention further relates to the medicinal composition, food or drink as described above wherein the disease or condition relating to autonomic nervous activity is selected from the group consisting of lowering of blood pressure, physical and mental tension, dry eye, dry mouth, immunomodulation failure, skin dysfunction and a lowering of blood sugar.

The invention further relates to the medicinal composition, food or drink as described above wherein the autonomic nervous control effect is an effect of reducing sympathetic nervous activity and/or an effect of enhancing parasympathetic nervous activity.

The invention further relates to the medicinal composition, food or drink as described above wherein the compound of the formula (1) is a compound represented by the following formula:

[Chemical formula 3]

and the autonomic nervous control effect is an effect of enhancing vagal (parasympathetic) nervous activity of the stomach. The invention further relates to the medicinal composition, food or drink as described above which contains a microorganism capable of producing the compound of the formula (1) or a processed product thereof. The invention further relates to the medicinal composition, food or drink as described above which contains a culture supernatant of a microorganism capable of producing the compound of the formula (1) or a processed product thereof. The invention further relates to the medicinal composition, food or drink as described above wherein the microorganism is a lactic acid bacterium. The invention further relates to the medicinal composition, food or drink as described above wherein the lactic acid bacterium is one belonging to the genus *Streptococcus, Lactobacillus, Leuconostoc, Pediococcus, Bifidobacterium, Tetragenococcus, Weissella, Enterococcus, Melisscoccus, Lactococcus, Carnobacterium, Vagococcus, Atopobium, Lactospheera, Oenococcus, Abiotrophia, Paralactobacillus, Granulicatella, Atopobactor, Alkalibacterium* or *Olsenella*, The invention further relates to the medicinal composition, food or drink as described above wherein the microorganism belongs to *Lactobacillus plantarum* (preferably *Lactobacillus plantarum* SAM 2446 strain (PERM ABP-10438), deposited at the International Patent Organism Depository (AIST Tsukuba Central 6, 1-1, Higashi 1-chome Tsukuba-shi, Ibaraki-ken 305-8566 Japan) on Oct. 26, 2005) or *Lactobacillus brevis* (preferably *Lactobacillus brevis* ATCC 14869, deoisuted at the American Type Culture Collection (10801 University Blvd, Manassas. VA 20110-2209) on. Oct. 25, 1962). The invention further relates to a method of producing the medicinal composition, food or drink as described above which comprises the step of culturing a microorganism capable of producing the compound of the formula (1) in a medium.

The invention further relates to the medicinal composition, food or drink as described above wherein the autonomic nervous control effect is one or more effects selected from the group consisting of an effect of enhancing sympathetic nervous activity of the kidney, an effect of reducing sympathetic nervous activity of the kidney and an effect of enhancing vagal (parasympathetic) nervous activity of the stomach, preferably an effect of reducing sympathetic nervous activity of the kidney and/or an effect of enhancing vagal (parasympathetic) nervous activity of the stomach.

The invention further relates to the medicinal composition, food or drink as described above wherein the autonomic nervous control effect is accompanied by a lowering of blood pressure.

The invention further relates to the medicinal composition, food or drink as described above, which has an effect of relieving allergic symptoms.

The invention further relates to the medicinal composition, food or drink as described above wherein a disease or condition relating to autonomic nervous activity is selected from the group consisting of cancer, stomach ulcer, ulcerative colitis, hypertension, pimple, backache, shoulder stiffness, knee pain and chronic rheumatoid arthritis.

The invention further relates to the medicinal composition, food or drink as described above wherein the phenyl lactic acid originates in a lactic acid bacterium and comprises D-phenyl lactic acid and L-lactic acid at a ratio of 5:1 to 0:1, preferably 1:1 to 1:20 and more preferably 1:1 to 1:10.

The invention further relates to the medicinal composition, food or drink as described above for treating allergic symptoms which contains D-phenyl lactic acid in an amount effective for enhancing the sympathetic nervous activity.

The invention further relates to the medicinal composition, food or drink as described above for treating a disease or condition selected from the group consisting of cancer, stomach ulcer, ulcerative colitis, hypertension, pimple, backache, shoulder stiffness, knee pain and chronic rheumatoid arthritis which contains D-phenyl lactic acid and/or L-phenyl lactic acid in an amount effective for reducing the sympathetic nervous activity.

The invention further relates to the medicinal composition, food or drink as described above for enhancing immune functions, lowering blood pressure, relaxing mind and body, promoting saliva secretion, promoting lacrimation, improving skin functions and/or lowering blood glucose level, which contains L-phenyl lactic acid in an amount effective for enhancing parasympathetic nervous activity.

The invention further relates to the medicinal composition as described above which is to be orally administered.

The invention further relates to an autonomic nervous controlling agent which contains phenyl lactic acid as the active ingredient.

The invention further relates to a blood pressure controlling agent which contains phenyl lactic acid as the active ingredient.

The invention further relates to use of phenyl lactic acid in producing a medicinal composition, a food or a drink for treating a disease or condition relating to autonomic nervous activity.

The invention further relates to a method of treating a disease or condition relating to autonomic nervous activity which comprises administering phenyl lactic acid.

The invention further relates to a method of controlling autonomic nervous activity which comprises administering phenyl lactic acid.

Phenyl lactic acid as used herein means a compound represented by the following formula (I):

[Chemical formula 4]

formula (I)

which is also called 2-hydroxy-3-phenyl propionic acid or β-3-phenyl lactic acid (MW 166.17). Phenyl lactic acid occurs as the following two isomers:

[Chemical formula 5]

D(+)-phenyl lactic acid
CAS7326-19-4 and

L(-)-3-phenyl lactic acid
CAS20312-36-1 i.e., D-phenyl lactic acid and L-phenyl lactic acid which are both known compounds. The mere term "phenyl lactic acid" as used herein involves either of the above D-phenyl lactic acid and L-phenyl lactic acid as a single compound and a mixture of them. It is known that phenyl lactic acid is contained in milk, cheese, honey and so on. Also, it is known that phenyl lactic acid is contained in microbial culture media. Further, standard preparations of D-phenyl lactic acid and L-phenyl lactic acid are marketed as reagents. Although phenyl lactic acid is a substance that is easily available as described above, and is highly safe, nothing but the antibacterial and antifungal effects thereof has been reported so far (Patent Document 5, Non-Patent Document 3). That is, no report has been made concerning the effect of phenyl lactic acid on the autonomic nervous activity or aiming at treating a disease or condition relating to the autonomic nervous activity with the use of phenyl lactic acid. The present inventors have found that a composition, a food or a drink (hereinafter sometimes referred to simply as "composition") containing phenyl lactic acid has an effect of controlling the autonomic nervous activity and is useful in treating a disease or condition relating to autonomic nervous activity.

As will be described in Examples hereinafter, the present inventors have found that phenyl lactic acid was contained in a culture supernatant remaining after culturing a lactic acid bacterium (*Lactobacillus plantum* SAM 2446 strain (FERM ABP-10438)) and L-phenyl lactic acid was the major component (D:L≡1:9).

To separate phenyl lactic acid from the above-described material, culture supernatant, etc., the starting material may be fractionated as such. Alternatively, it may be concentrated by freeze drying, liquid-liquid partition using an organic solvent or the like prior to the fractionation. The subsequent fractionation procedure may be carried out by, if desired, conducting crude fractionation by ultrafiltration or the like followed by a treatment with the use of a reversed phase column, an optical resolution column, etc. The liquid-liquid partition, ultrafiltration, reversed phase column treatment, optical resolution column treatment, etc. as described above can be conducted by methods commonly employed by a person skilled in the art. The phenyl lactic acid obtained by the fractionation may be a mixture of D-phenyl lactic acid with phenyl lactic acid or each single compound. In the case where a mixture is obtained, it may be optically resolved, if desired, to give each single compound.

The formation of phenyl lactic acid by the above method can be confirmed by, for example, comparing with a standard or MS spectrometry or NMR spectrometry.

Alternatively, use may be made of a marketed standard preparation of phenyl lactic acid (manufactured by BACHEM, etc.). It is also possible to obtain phenyl lactic acid by synthesis. The synthesis method is not particularly restricted.

Phenyl lactic acid contained in the composition according to the present invention may be used in the form of a pharmaceutically acceptable salt such as hydrochloride or in the form of a salt (a prodrug) that is converted into phenyl lactic acid in vivo.

The present invention also provides the medicinal composition, food or drink as described above which contains a microorganism capable of producing phenyl lactic acid (the compound of the formula (I)) or a processed product of the same, or a culture supernatant of this microorganism or a processed product of the same.

The expression "capable of producing phenyl lactic acid" as used herein means capable of producing phenyl lactic acid when cultured under effective conditions. Such effective conditions can be appropriately determined by a person skilled in the art. The capability of producing phenyl lactic acid of a microorganism can be confirmed by analysis of the microorganism (including a microorganism per se, dried cells of a microorganism, a culture medium of a microorganism, an extract of a microorganism and so on) by use of a commonly employed procedure such as LC, MS or NMR to examine the presence of phenyl lactic acid, etc. A microorganism capable of producing phenyl lactic acid in the case of appropriately controlling the culture conditions (the culture composition, culture temperature, culture pH, culture density, etc.) also falls within the scope of the microorganism capable of producing phenyl lactic acid.

The microorganism as described above may be collected from a natural source. Moreover, a variant and/or a recombinant designed as being capable of producing phenyl lactic acid are also included in the scope of the present invention. A variant and/or a recombinant designed as showing elevated phenyl lactic acid productivity compared with a wild strain when cultured in a culture medium of the same composition also fall within the scope.

The phenyl lactic acid produced by the microorganism as described above may be D-phenyl lactic acid, L-phenyl lactic acid or a mixture thereof. As will be described in Examples hereinafter, for example, a microorganism capable of producing desired phenyl lactic acid may be optionally selected and employed depending on the disease or condition to be treated.

The microorganism capable of producing phenyl lactic acid may be, for example, a lactic acid bacterium, a yeast, a hay *bacillus* or the like. Examples of the lactic acid bacterium include microorganisms belonging to the genus *Streptococcus, Lactobacillus, Leuconostoc, Pediococcus, Bifidobacterium, Tetragenococcus, Weissella, Enterococcus, Melisscoccus, Lactococcus, Carnobacterium, Vagococcus, Atopobium, Lactosphaera, Oenococcus, Abiotrophia, Paralactobacillus, Granulicatella, Atopobactor, Alkalibacterium* or *Olsenella*; examples of the yeast include microorganisms belonging to the genus *Candida* or *Saccharomyces*; and examples of the hay *bacillus* include microorganisms belonging to *Bacillus subtilis*.

Preferable examples of the microorganism include some strains belonging to *Lactobacillus plantarum, Lactobacillus alimentariu, Lactobacillus rhamnosus, Lactobacillus sanfranciscensis, Lactobacillus hilgardii, Leuconostoc citreum* and *Lactobacillus brevis*, some strains of *Lactobacillus acidophilus, Leuconostoc mesenteroides* subsp. *mesenteroides* and *Enterococcus faecalis* described in Patent Document 5. Particularly preferable microorganisms are *Lactobacillus plantarum* (more specifically *Lactobacillus plantarum* SAM 2446 strain (FERM ABP-10438)) and *Lactobacillus brevis* (more specifically *Lactobacillus brevis* ATCC 14869).

The present invention further provides a method of producing the medicinal composition, food or drink as described above which comprises the step of culturing the above-described microorganism capable of producing phenyl lactic acid in a medium. The microorganism can be cultured by inoculation of an appropriate medium with the microorganism and employing of a culture procedure that is well known to a person skilled in the art, depending on the kind of the microorganism.

Next, the culture in the case where the microorganism is a lactic acid bacterium will be briefly described by way of example. As the medium, use can be made of, for example, an agar medium and/or a liquid medium. To the medium, a carbon source and a nitrogen source well known to a person skilled in the art are optionally added each at a desired concentration. If necessary, trace nutrients such as an inorganic ion and a vitamin may be further added. More conveniently, use can be made of a marketed medium such as MRS medium to which additives may be optionally added. In the culture, a treatment for increasing the phenyl lactic acid yield may be optionally conducted by using a procedure that is well known by a person skilled in the art. For example, phenylalanine may be added in culturing a microorganism belonging to the genus *Lactobacillus* to increase the phenyl lactic acid contained in the medium, as reported in Non-Patent Document 3. After preparation of the medium, it is adjusted to pH 6.0 to 7.0 with the use of an appropriate acid or base and then sterilized by use of an autoclave or the like.

Subsequently, the medium is inoculated with the lactic acid bacterium. Then, the microorganism can be proliferated in the medium by shaken culture, static culture, industrial-scaled culture in a tank, solid culture in a solid medium such as an agar medium, etc. while the culture temperature is controlled to 10° C. to 45° C. usually for 1 to 2 days. The culture conditions vary depending on the microorganism employed. In the case of using *Lactobacillus plantarum*, for example, static culture can be conducted in MRS medium of around pH 6.5 at around 37° C. for 1 day. The microorganism thus cultured is centrifuged if desired, and then filtered if necessary. Thus, a culture supernatant can be obtained.

As will be shown in Examples hereinafter, D-phenyl lactic acid and L-phenyl lactic acid each affects the rat kidney sympathetic nervous activity, blood pressure and the stomach vagal (parasympathetic) nervous activity when transduodenally administered to rats each as a single compound.

Concerning the kidney sympathetic nervous activity, more specifically, when administered in a dose of 10 µg/animal, D-phenyl lactic acid showed an effect of enhancing kidney sympathetic nervous activity while L-phenyl lactic acid showed little effect on kidney sympathetic nervous activity. At a dose of 100 µg/animal, both of D-phenyl lactic acid and L-phenyl lactic acid showed an effect of reducing kidney sympathetic nervous activity.

Concerning blood pressure, both of L-phenyl lactic acid and D-phenyl lactic acid showed a hypotensive effect at a dose of 100 µg.

Concerning stomach vagal (parasympathetic) nervous activity, L-phenyl lactic acid showed an effect of enhancing stomach vagal (parasympathetic) nervous activity at a dose of 100 µg/animal.

As methods for evaluating autonomic nervous activity, there can be enumerated biophysical measurement methods using, for example, an electrocardiograph, a sphygmomanometer, a galvanic skin reflex meter or a pupil meter and biochemical methods of measuring blood catecholamine concentration, etc. Although analysis on heart rate change using an electrocardiograph is a commonly employed method, the present inventors evaluated the effects of phenyl lactic acid on autonomic nervous activity by a method using rats, as will be shown in Examples hereinafter, whereby the effects of the administered substance on the autonomic nervous activity can be directly evaluated. This method is characterized in that the effects of the administered substance on the autonomic nervous activity controlling individual organs, tissues and so on can be separately examined. Moreover, this method has a merit that the autonomic nervous control functions of different substances can be successively evaluated so long as the test animal survives.

The following table shows organs, hormones and vital actions seemingly participating in autonomic nervous actions, possible effects of the autonomic nerve thereon, and examples of the expected effects.

TABLE 1

| | | Sympathomimetic | Parasympathomimetic |
|---|---|---|---|
| Pancreas | Insulin | Decrease | Increase |
| | Glucagon | Increase | Decrease |
| Adrenal gland | Blood glucose | Increase | Decrease |
| | Blood pressure | Increase | Decrease |
| Liver | Glycogen | Decomposition | Synthesis |
| | Sugar | Gluconeogenesis →Sugar synthesis | Glycolysis enhancement →Sugar use promotion |
| Kidney | Blood pressure | Increase | Decrease |
| Stomach | Digestion/absorption | Decrease →Loss of appetite (antiobesity) | Promotion →Appetite enhancement |
| Skin | Blood flow rate | Decrease | Increase →Moisturization enhancement (cosmetic) |
| Immunity | | Decrease | Increase →NK activity rise |
| Pupil | | Enlargement | Contraction |
| Heart rate | | Increase | Decrease |
| Cardiovascular system | | Enhancement (facial pallor) | Regulation (facial flush) |
| Sweat and saliva | | Secretion regulation | Secretion enhancement |

As the above table clearly shows, the autonomic nervous activity closely affect various controlling mechanisms in vivo, for example, blood sugar control, blood pressure control, hormone secretion control, sugar metabolism control, gastric juice secretion control, blood flow rate control, body temperature control and so on. Disturbance of the balance in autonomic nervous activity leads to health troubles such as indefinite complaint. Indefinite complaint involves various symptoms such as general fatigue, sleep disorder, palpitation, thirst (dry mouth), sexual impotence, dryness in the oral cavity, eye fatigue and so on (Non-Patent Document 2). Examples of sympathetic predominant diseases include cancer, stomach ulcer, ulcerative colitis, hypertension, pimple, backache, shoulder stiffness, knee pain, chronic rheumatoid arthritis and so on. Examples of excessive parasympathetic predominant diseases include allergic symptoms occurring as a result of hypersensitive reaction of proliferated lymphocytes with antigens. It is expected that the enhancement of parasympathetic nervous activity brings about effects of improving immune functions due to an increase in lymphocytes, lowering blood pressure, relaxing mind and body, promoting saliva secretion, promoting lacrimation, lowering blood glucose level and cosmetic and skin-care effects induced by the improvement in skin functions.

The term "autonomic nervous control effect" as used herein includes an effect of enhancing sympathetic nervous activity, an effect of reducing sympathetic nervous activity enhancement, an effect of reducing sympathetic nervous activity, an effect of enhancing parasympathetic nervous activity, an effect of reducing parasympathetic nervous activity enhancement and an effect of reducing parasympathetic nervous activity.

Because of containing phenyl lactic acid as described above, the composition according to the present invention is usable in treating a disease or condition relating to the autonomic nervous activity. For example, it is usable in treating symptoms frequently occurring due to autonomic nervous disorders and sometimes called indefinite complaint in general, such as shortness of breath, palpitation, shoulder stiffness, headache, vertigo, anxiety, loss of appetite, lassitude, sleep disorder, etc. (also called autonomic imbalance), and menopausal syndrome due to body temperature control failure seemingly caused by autonomic nervous disorders (for example, dizziness, hot flash, coldness, sudden perspiration, etc.). It seems particularly usable in treating diseases or conditions that can be treated by reducing sympathetic nervous activity, for example, sympathetic predominant diseases (for example, anthrophobia, erythrophobia, excessive sweating, palpitation, arrhythmia, diarrhea, postural hypotension, gastric digestion failure, fatigue, cancer, stomach ulcer, ulcerative colitis, hypertension, pimple, backache, shoulder stiffness, knee pain, chronic rheumatoid arthritis and so on) and parasympathetic predominant diseases (for example, allergic symptoms occurring as the results of hypersensitive reaction of proliferated lymphocytes with antigens). It is also considered that the composition according to the present invention is useful in treating hypertension. It is also considered that the composition according to the present invention can enhance parasympathetic nervous activity and thus increase lymphocytes, thereby exerting effects of enhancing immune functions, lowering blood pressure, relaxing mind and body, promoting saliva secretion, promoting lacrimation, lowering blood glucose level, etc., which makes it useful in lowering blood pressure and treating mind and body tension, dry eye, dry mouth, immunomodulation failure, blood glucose lowering, etc.

The expression "to treat a disease or condition" as used herein means to prevent worsening of the disease or condition, to relieve the disease or condition and to prevent the disease or condition. Based on the results of Examples as will be described hereinafter, it is determined that a sufficient effect can be obtained by administering the composition according to the present invention, which contains phenyl lactic acid as described above, containing 5 µg/kg or more of phenyl lactic acid. Although there is no upper limit of the administration dose of phenyl lactic acid, it is generally favorable that the dosage of phenyl lactic acid does not exceed about 50 mg/kg from the viewpoint of the characteristic smell thereof, and in view of cost. To fully achieve the effect, it is desirable that the composition according to the present invention contains from 5 µg/kg to 50 mg/kg per dose (preferably from 10 µg/kg to 20 mg/kg and more preferably from 20 µg/kg to 10 mg/kg) of phenyl lactic acid. More specifically, it is desirable that the composition according to the present invention contains from 300 µg to 3000 mg (preferably from 600 µg to 1200 mg and more preferably from 1200 µg to 600 mg) per dose of phenyl lactic acid in the case of administering to an adult human. It is possible that the composition according to the present invention contains from 0.5 µg to 5 mg (preferably from 1 µg to 2 mg and more preferably from 2 µg to 1 mg) of phenyl lactic acid per product weight (g). From another viewpoint, it is possible that the composition according to the present invention contains 4 µg or more (preferably 25 µg or more and more preferably 75 µg or more) of phenyl lactic acid per product weight (g). In each case, the upper limit may be adjusted to, for example, 1 mg, 2 mg or 5 mg per product weight (g).

The dose of D-phenyl lactic acid and/or L-phenyl lactic acid can be appropriately determined depending on the disease or condition to be treated by reference to, for example, Examples as will be described hereinafter. The expression "clinically effective amount" as used herein means an amount clinically effective in controlling the autonomic nervous activity. The expression "amount effective for enhancing sympathetic nervous activity" means an amount effective for enhancing sympathetic nervous activity. The expression "amount effective for reducing sympathetic nervous activity" means an amount effective for reducing sympathetic nervous activity. The expression "amount effective for enhancing parasympathetic nervous activity" means an amount effective for enhancing parasympathetic nervous activity. These effective amounts can be determined by using as an indication the effect of a substance on autonomic nervous activity and the dose at which the effect is achieved, measured by, for example, the methods as will be described in Examples hereinafter.

In the composition according to the present invention, use can be made of a material containing phenyl lactic acid, a microorganism capable of producing phenyl lactic acid, a culture supernatant of the microorganism, a culture containing the microorganism, etc. either as such or after isolation and purification via extraction, fractionation or the like, though the present invention is not particularly restricted thereto. It is also possible to use a processed product such as a concentrate or a dry powder obtained by treating such a material as described above by using a commonly employed procedure such as sterilization, vacuum concentration, freeze drying or the like. In the case of a concentrate which can be hardly powdered by drying, it may be mixed with an excipient commonly employed in the art such as dextrin, a high-molecular starch hydrolyzate or a high-molecular peptide, and then powdered by drying. From the viewpoints of handling properties and storage properties, a powdered composition is preferred.

The composition according to the present invention can be processed into various forms such as foods and drinks (including foods, drinks, seasonings, alcoholic drinks, functional foods and so on) and medicinal compositions. For example, it is possible to provide a food, a drink or a medicine with the use of phenyl lactic acid, a microorganism capable of producing phenyl lactic acid, a culture supernatant of the microorganism, a processed product thereof and so on.

Examples of the foods and drinks provided by the present invention include various ones such as candies, troches, yogurts, ice creams, puddings, jellies, mizu-yokan (adzuki bean jelly), alcoholic drinks, coffee drinks, juices, fruit drinks, carbonated drinks, soft drinks, milk, milk serum drinks, lactic acid drinks and so on.

These foods and drinks can be prepared by conventional methods with the use of various additives if needed. More specifically, these foods and drinks can be produced by blending of appropriate materials commonly employed in foods such as glucose, fructose, sucrose, maltose, sorbitol, stevioside, rubusoside, corn syrup, lactose, citric acid, tartaric acid, malic acid, succinic acid, lactic acid, ascorbic acid, dl-α-tocopherol, sodium erythorbate, glycerol, propylene glycol, a glycerol fatty acid ester, a polyglycerol fatty acid ester, a sucrose fatty acid ester, a sorbitan fatty acid ester, a propylene glycol fatty acid ester, acacia, carrageenan, casein, gelatin, pectin, agar, vitamin Bs, nicotinamide, calcium panthothenate, amino acids, calcium salts, a colorant, a perfume, a preserver and so on.

The medicines provided by the present invention may be in various dosage forms that are prepared by conventional methods with the use of various additives if needed. For example, it is possible to provide medicines for oral administration such as tablets, capsules, granules, powder, syrups and extracts and medicines for parenteral administration such as ointments, eye ointments, lotions, creams, patches, suppositories, eye drops, nasal drops and injections.

These medicines may be produced by conventional methods with the use of various additives. Any additives commonly employed in the art can be used without specific restriction. Examples thereof include solid carriers such as starch, lactose, sucrose, mannitol, carboxymethylcellulose, corn starch and inorganic salts; liquid carriers such as distilled water, physiological saline, aqueous glucose solution and alcohols such as ethanol, propylene glycol and polyethylene glycol; and oily carriers such as various animal or vegetable oils, white vaseline, paraffin and waxes.

The composition according to the present invention contains phenyl lactic acid as the active ingredient, optionally together with other active ingredient(s) commonly employed in medicinal compositions, foods and drinks.

For example, the composition according to the present invention may contain one member or a combination of two or more members selected from among a substance having an autonomic control effect (a sympathetic agents, a parasympathetic agents, etc.), a substance having an effect of enhancing sympathetic nervous activity, a substance relating to the treatment of allergic symptoms, a substance having an effect of reducing sympathetic nervous activity, a substance relating to the treatment of a disease or condition selected from the group consisting of cancer, stomach ulcer, ulcerative colitis, hypertension, pimple, backache, shoulder stiffness, knee pain and chronic rheumatoid arthritis, a hypotensive substance, a substance having an effect of enhancing parasympathetic nervous activity (including a substance having an aroma therapy effect and a relaxing effect), a substance enhancing immune functions, lowering blood pressure, relaxing mind and body, promoting saliva secretion, promoting lacrimation, improving skin functions and/or lowering blood glucose level and so on that are well known to a person skilled in the art.

In the case of the composition according to the present invention containing a microorganism capable of producing phenyl lactic acid, a processed product thereof, a culture supernatant thereof or a processed product thereof, it may contain, in particular, the above-described substances with microbial origin (a substance having an autonomic nerve control effect, a substance having an effect of enhancing sympathetic nervous activity, a substance having an effect of reducing sympathetic nervous activity, a hypotensive substance, a substance having an effect of enhancing parasympathetic nervous activity, etc.).

In the case where the composition according to the present invention contains D-phenyl lactic acid in an amount effective for enhancing sympathetic nervous activity, it is particularly preferable that the other active ingredient as discussed above is a substance having an effect of enhancing sympathetic nervous activity or a substance relating to allergic symptoms. In a case where the composition according to the present invention contains D-phenyl lactic acid and/or L-phenyl lactic acid in an amount effective for enhancing sympathetic nervous activity, it is particularly preferable that the other active ingredient as discussed above is a substance having an effect of enhancing sympathetic nervous activity, or a substance relating to the treatment of a disease or condition selected from the group consisting of cancer, stomach ulcer, ulcerative colitis, hypertension, pimple, backache, shoulder stiffness, knee pain and chronic rheumatoid arthritis. In the case where the composition according to the present invention contains L-phenyl lactic acid in an amount effective for enhancing parasympathetic nervous activity, it is particularly preferable that the other active ingredient as discussed above is a substance having an effect of enhancing parasympathetic nervous activity, a substance enhancing immune functions, lowering blood pressure, relaxing mind and body, promoting saliva secretion, promoting lacrimation, improving skin functions and/or lowering blood glucose level and so on.

In the medicinal composition, food or drink according to the present invention, indication may be made of a specific purpose of use (for example, controlling the autonomic nervous activity, controlling the sympathetic nervous activity, controlling the parasympathetic nervous activity, relieving allergic symptoms, treating/preventing hypertension, enhancing immune functions, relaxing mind and body, lowering blood sugar, promoting saliva secretion, promoting lacrimation, achieving cosmetic and skin-care effects, maintaining health, etc.) and/or a specific way of use (for example, dose, dosing frequency and dosing method).

Effects of the Invention

As discussed above in detail, the present invention provides a medicinal composition, a food or a drink for controlling the autonomic nervous activity per se that are the fundamental factors causative of a disease or condition relating to the autonomic nervous activity. In particular, it provides the medicinal composition, food or drink as described above which has a high safety and can be conveniently produced without causing a rise in blood pressure.

EXAMPLES

Now, the present invention will be described in greater detail by reference to the following Examples, though the present invention is not restricted thereto.

In Example 1, the chirality of phenyl lactic acid contained in a culture supernatant of *Lactobacillus plantarum* SAM 2446 strain (FERM ABP-10438) was analyzed. In Examples 2 to 4, the effects of phenyl lactic acid-containing compositions on rat autonomic nervous activity were examined by using an L-phenyl lactic acid reagent (L-β-3-phenyl lactic acid (Q1375)) and a D-phenyl lactic acid reagents (D-β-3-phenyl lactic acid (Q1670) manufactured by BACHEM.

Example 1

Confirmation of Chirality of Phenyl Lactic Acid (2-hydroxy-3-phenyl propionic acid) in Culture Supernatant of *Lactobacillus plantarum* SAM 2446 Strain (FERM ABP-10438)

Starting with a freeze dried culture supernatant obtained by culturing *Lactobacillus plantarum* SAM 2446 strain, a peak assignable to phenyl lactic acid was collected by using Develosil C30-UG-5 column. Next, this peak was dissolved in hexane containing 0.1% of TFA and 5% of 2-propanol and loaded on Chiral Pack AD (manufactured by DAICEL CHEMICAL INDUSTRIES, Ltd.). Then, isocratic analysis was conducted using hexane containing 0.1% of TFA and 5% of 2-propanol as a mobile phase.

Figure 1:
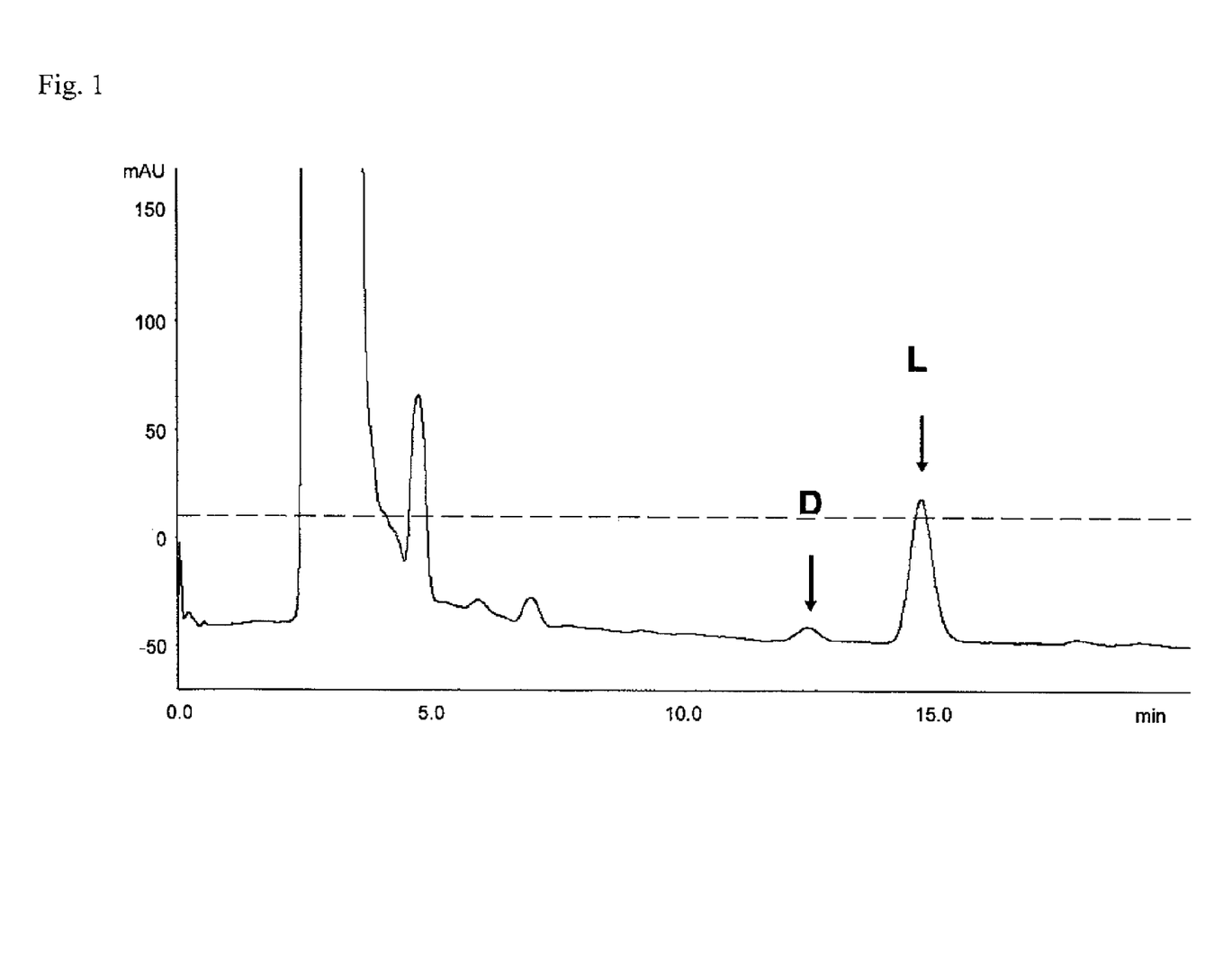
FIG. 1 presents a chart whereby the chirality of 2-phenyl lactic acid in the lactic acid culture supernatant of Example 1 is confirmed.

As a result, it was clarified that the phenyl lactic acid in the culture supernatant of *Lactobacillus plantarum* SAM 2446 strain comprised L-phenyl lactic acid as the major component (D:L≈1:9) (FIG. 1). The yield was about 90%.

Example 2

Effect of L-Phenyl Lactic Acid or D-Phenyl Lactic Acid on Rat Kidney Sympathetic Nervous Activity In these experiments, use was made of male Wister rats weighing about 300 to 350 g which had been preliminarily fed in a thermostatic chamber (24° C.) with a light-dark cycle of 12-hour intervals (under illumination from 8:00 to 20:00) for 1 week or longer. A single rat was employed for each nervous experiment. The animals were fed with a feed (MF: Oriental Yeast) and water ad libitum. The autonomic nervous activity were examined by fasting the rats for 5 hours on the day of the experiment and then subjecting to an abdominal surgery under urethane-anesthesia (1 g/kg, i.p.). Then, the effects of the transduodenal administration of L-phenyl lactic acid and D-phenyl lactic acid (10 μg or 100 μg) on the kidney sympathetic nervous activity were measured in accordance with the method reported by T. Yamano et al., Neurosci. Lett. 313:78-82 (2001), A. Niijima et al., Autonom. Neurosci.: Basic & Clinical 97:99-102 (2002) and M. Tanida et al., Am. J. Physiol: Regulatory, Integrative and Comparative Physiology 288:R447-R455 (2005). Namely, the sympathetic nerve projecting toward the kidney was cut before the organ and the central side was placed on a silver electrode. Thus, a change in the electrical activity was monitored. To prevent dryness, the electrode had been preliminarily dipped in a mixture of liquid paraffin and petroleum jelly for a sufficient period of time. From the initiation of the surgery to the completion of the measurement, a tube was inserted into the respiratory tract for the management of the airway. The body temperature (rat rectal temperature) was maintained at 35±0.5° C. with the use of a heater. The transduodenal administration was conducted by dissolving L-phenyl lactic acid or D-phenyl lactic acid in physiological saline to give a concentration of 10 μg/2 ml or 100 μg/2 ml, and administering 2 ml/animal of each solution at a rate of 1 ml/min through a polyethylene tube inserted into the duodenum. Electrical nervous activity thus obtained were amplified with a condenser type differential amplifier, monitored with an oscilloscope and recorded on a magnetic tape. To separate the raw data from the background noise, all of the nervous activities were converted into standard pulses by use of a slicer and a window discriminator before analyzing.

Discharge frequencies were indicated on a pen recorder by using a rate meter at a reset time of 5 seconds. The data was analyzed based on the average discharge frequency per 5 seconds (pulse/5 sec) and expressed in percentage by referring the level before the administration as to 100%. A group with the administration of physiological saline was employed as a control.

Figure 2:
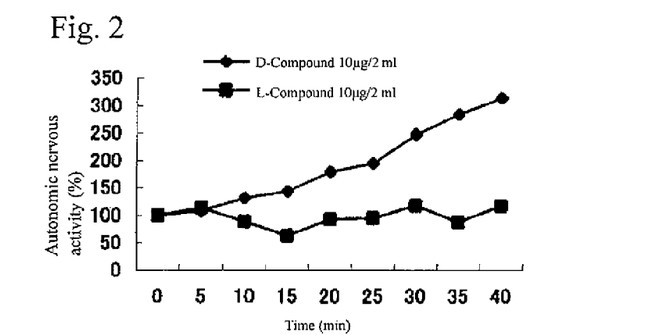
FIG. 2 is a graph which shows the effects of the administration of 10 μg portions of L-phenyl lactic acid and D-phenyl lactic acid on rat kidney sympathetic nervous activity observed in Example 2.
Figure 3:
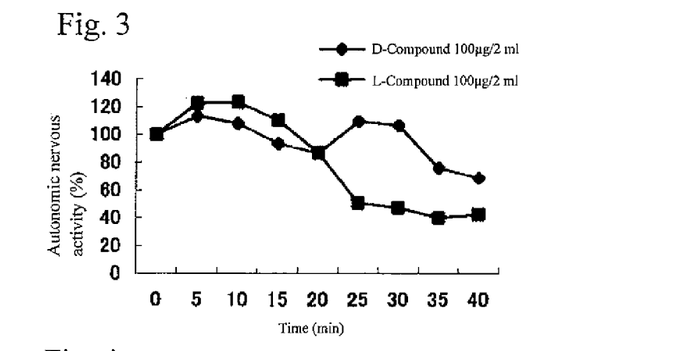
FIG. 3 is a graph which shows the effects of the administration of 100 μg portions of L-phenyl lactic acid and D-phenyl lactic acid on rat kidney sympathetic nervous activity observed in Example 2.

As a result, the control group showed no effect on all of autonomic nervous activity examined and blood pressure. In the administration group, on the other hand, kidney sympathetic nervous activity was enhanced by the administration of 10 μg of D-phenyl lactic acid while L-phenyl lactic acid exerted little effect on the kidney sympathetic nervous activity (FIG. 2). When administered in a dose of 100 μg, both of D-phenyl lactic acid and L-phenyl lactic acid reduced kidney sympathetic nervous activity and L-phenyl lactic acid showed a higher reducing effect (FIG. 3).

Example 3

Figure 4:
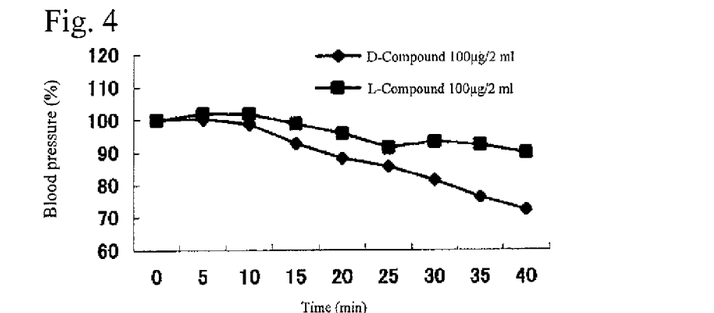
FIG. 4 is a graph which shows the effects of the administration of 100 μg portions of L-phenyl lactic acid and D-phenyl lactic acid on rat blood pressure observed in Example 3.

Effect of L-Phenyl Lactic Acid or D-Phenyl Lactic Acid on Rat Blood Pressure The procedure of Example 2 was followed and thus the effects of the transduodenal administration (10 μg or 100 μg) of L-phenyl lactic acid and D-phenyl lactic acid on rat blood pressure were examined in accordance with the methods reported in the documents cited in Example 2. A cannula was inserted into the left femoral artery and then the blood pressure was measured by use of a transducer. A single rat was employed for each nervous experiment. The transduodenal administration was conducted as in Example 2. As a result, it was clarified that both of L-phenyl lactic acid and D-phenyl lactic acid showed hypotensive effects at an administration dose of 100 μg (FIG. 4).

Example 4

Figure 5:
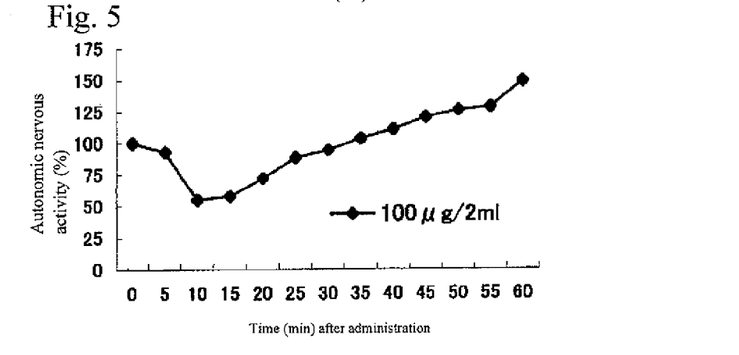
FIG. 5 is a graph which shows the effects of the administration of 100 μg of L-phenyl lactic acid on rat stomach vagal (parasympathetic) nervous activity observed in Example 4.

Effect of L-Phenyl Lactic Acid on Rat Stomach Vagal (Parasympathetic) Nervous Activity The procedure of Example 2 was followed and thus the effect of the transduodenal administration of 100 mg of L-phenyl lactic acid on rat stomach vagal (parasympathetic) nervous activity was examined. As a result, enhancement of rat stomach vagal (parasympathetic) nervous activity was observed (FIG. 5).

Production Example 1

Phenyl Lactic Acid-Containing Medicine

Tablet:

A phenyl lactic acid-containing medicine (tablets) was produced by the following method.

5 g of marketed phenyl lactic acid, 293.7 g of lactose and 1.3 g of magnesium stearate were mixed together and tabletted with a single-shot tabletting machine to give tablets, each being 10 mm in diameter and 300 mg in weight.

Granules:

5 g of marketed phenyl lactic acid was added to 293.7 g of lactose and 1.3 g of magnesium stearate and the mixture was compressed, powdered, dressed and sieved to give granules of 20-50 mesh.

Production Example 2

Phenyl Lactic Acid-Containing Food and Drink

Various phenyl lactic acid-containing foods and drinks of the following compositions were produced by conventional methods.

| (Component) | (Part by weight) |
|---|---|
| Ice cream: | |
| Fresh cream (fat: 45%) | 33.8 |
| Skim milk powder | 11.0 |
| Granulated sugar | 14.8 |
| Sugar-containing yolk | 0.3 |
| Vanilla essence | 0.1 |
| Water | 39.995 |
| Phenyl lactic acid | 0.005 |
| Total | 100.00 |
| Juice: | |
| Unshu orange juice concentrate (frozen) | 5.0 |
| High-fructose corn syrup | 11.0 |
| Citric acid | 0.2 |
| L-Ascorbic acid | 0.02 |
| Phenyl lactic acid | 0.005 |
| Perfume | 0.2 |
| Colorant | 0.1 |
| Water | 83.475 |
| Total | 100.00 |
| Lactic acid drink: | |
| Fermented milk (solid milk content: 21%) | 14.76 |
| High-fructose corn syrup | 13.31 |
| Pectin | 0.5 |
| Citric acid | 0.08 |
| Perfume | 0.15 |
| Water | 71.195 |
| Phenyl lactic acid | 0.005 |
| Total | 100.00 |
| Yogurt: | |
| Fresh milk (fat: 3.4%) | 80.0 |
| Fresh cream (fat: 50%) | 8.0 |
| Skim milk powder | 1.5 |
| Water | 7.495 |
| Starter | 3.0 |
| Phenyl lactic acid | 0.005 |
| Total | 100.00 |
| Coffee drink: | |
| Granulated sugar | 8.0 |
| Skim milk powder | 5.0 |
| Caramel | 0.2 |
| Coffee extract | 2.0 |
| Perfume | 0.1 |
| Polyglycerol fatty acid ester | 0.05 |
| Sodium chloride | 0.05 |
| Water | 84.595 |
| Phenyl lactic acid | 0.005 |
| Total | 100.00 |
| Alcoholic drink: | |
| 50 vol. % ethanol | 32.0 |
| Sugar | 8.4 |
| Fruit juice | 2.4 |
| Phenyl lactic acid | 0.005 |
| Purified water | 57.195 |
| Total | 100.00 |

Discussion

Based on these results, it was found that the culture supernatant of *Lactobacillus plantarum* SAM 2446 strain contained phenyl lactic acid in the form of optical isomers L-phenyl lactic acid and D-phenyl lactic acid, and L-phenyl lactic acid was the major component.

When the effects of these compounds on kidney sympathetic nervous activity were examined, D-phenyl lactic acid showed an effect of enhancing kidney sympathetic nervous activity at an administration dose of 10 μg/animal while L-phenyl lactic acid showed little effect on kidney sympathetic nervous activity. Thus, it is considered that at an effective amount at a low concentration, D-phenyl lactic acid is efficacious against allergic symptoms that are parasympathetic predominant diseases occurring as results of hypersensitive reaction of proliferated lymphocytes with antigens. At an administration dose of 100 μg/animal, both of D-phenyl lactic acid and L-phenyl lactic acid showed an effect of reducing kidney sympathetic nervous activity. Thus, it is considered that in an effective amount at a high concentration, L-phenyl lactic acid and D-phenyl lactic acid are efficacious against sympathetic predominant diseases such as cancer, stomach ulcer, ulcerative colitis, hypertension, pimple, backache, shoulder stiffness, knee pain and chronic rheumatoid arthritis, etc.

Because they have a hypotensive effect, it is considered that L-phenyl lactic acid and D-phenyl lactic acid are efficacious in relieving hypertension.

Moreover, it was indicated that L-phenyl lactic acid showed an effect of enhancing the stomach vagal (parasympathetic) nervous activity in an administration dose of 100 μg/animal, which suggests that it has an effect of enhancing parasympathetic nervous activity. Based on this result, it is expected that L-phenyl lactic acid is efficacious in improving immune functions due to an increase in lymphocytes, lowering blood pressure, relaxing mind and body, promoting saliva secretion, promoting lacrimation, improving skin functions, lowering blood glucose level and so on.

The invention claimed is:

1. A method for treating or improving a condition or a disease comprising:
    administering a medicinal composition, a food, or a drink which contains 75 micrograms or more of a compound represented by the following formula (1):

[Chemical formula 1]

per gram of the composition, the food or the drink, and a pharmaceutically or nutritionally acceptable additive to a subject in need thereof,
    wherein the compound of formula (1) comprises at least one of D-phenyl lactic acid and L-phenyl lactic acid,
    wherein an amount of L-phenyl lactic acid contained in the composition, the food, or the drink is higher than an amount of D-phenyl lactic acid,
    wherein the composition, the food, or the drink has an effect of enhancing parasympathetic nervous activity, and
    wherein the condition or the disease is one that can be treated or improved by enhancing parasympathetic nervous activity of the subject.

2. The method as claimed in claim 1,
    wherein the disease or condition is selected from the group consisting of high blood pressure, physical and mental tension, dry eye, dry mouth, immunomodulation failure, skin dysfunction and a high blood sugar.

3. The method as claimed in claim 1, wherein the composition, the food, or the drink contains a microorganism capable of producing the compound of the formula (1) or a processed product thereof.

4. The method as claimed in claim 1, wherein the composition, the food, or the drink contains a culture supernatant of a microorganism capable of producing the compound of the formula (1) or a processed product thereof.

5. The method as claimed in claim 1 wherein the microorganism is a lactic acid bacterium.

6. The method claimed in claim 5 wherein the lactic acid bacterium is one belonging to the genus *Streptococcus, Lactobacillus, Leuconostoc, Pediococcus, Bifidobacterium, Tetragenococcus, Weissella, Enterococcus, Melisscoccus, Lactococcus, Carnobacterium, Vagococcus, Atopobium, Lactosphaera, Oenococcus, Abiotrophia, Paralactobacillus, Granulicatella, Atopobactor, Alkalibacterium* or *Olsenella*.

7. The method as claimed in claim 5 wherein the microorganism belongs to *Lactobacillus plantarum* or *Lactobacillus brevis*.

8. The method as claimed in claim 7, wherein the microorganism belongs to *Lactobacillus plantarum* SAM 2446 strain (FERM BP-10438) or *Lactobacillus brevis* ATCC 14869.

9. The method as claimed in claim 7, wherein the microorganism belongs to *Lactobacillus plantarum* SAM 2446 strain (FERM BP-10438).

10. The method as claimed in claim 1, wherein a ratio of the amount of L-phenyl lactic acid to the amount of D-phenyl lactic acid is more than 1 and not more than 20.

11. The method as claimed in claim 1, wherein the compound of formula (1) is a product produced by *Lactobacillus plantarum* SAM 2446 strain (FERM BP-10438).

* * * * *